US006365132B1

(12) United States Patent
Litkowski et al.

(10) Patent No.: US 6,365,132 B1
(45) Date of Patent: Apr. 2, 2002

(54) METHODS AND COMPOSITIONS FOR WHITENING TEETH

(75) Inventors: Leonard J. Litkowski, Baltimore; Gary D. Hack, Columbia, both of MD (US); David C. Greenspan, Gainesville, FL (US)

(73) Assignees: Univ. of MD., Baltimore, Baltimore, MD (US); USBiomaterials Corp., Alachus, FL (US)

( * ) Notice: Subject to any disclaimer, the term of this patent is extended or adjusted under 35 U.S.C. 154(b) by 0 days.

(21) Appl. No.: 09/527,721

(22) Filed: Mar. 17, 2000

Related U.S. Application Data

(63) Continuation of application No. PCT/US98/18500, filed on Sep. 18, 1998.
(60) Provisional application No. 60/059,222, filed on Sep. 18, 1997.

(51) Int. Cl.$^7$ .............. A61K 7/16; A61C 5/00; C03C 3/078
(52) U.S. Cl. .......... 424/49; 106/35; 433/217.1; 433/228.1
(58) Field of Search ................ 424/49–58

(56) References Cited

U.S. PATENT DOCUMENTS

| | | |
|---|---|---|
| 3,981,736 A | 9/1976 | Broemer et al. |
| 4,057,621 A | 11/1977 | Pashley et al. |
| 4,239,113 A | 12/1980 | Gross et al. |
| 4,538,990 A | 9/1985 | Pashley |
| 4,605,415 A | 8/1986 | Richez |
| 4,632,826 A | 12/1986 | Plöger et al. |
| 4,775,592 A | 10/1988 | Akahane et al. |
| 4,775,646 A * | 10/1988 | Hench et al. ............. 501/2 |
| 4,783,429 A | 11/1988 | Shibuya et al. |
| 4,822,599 A | 4/1989 | Mitra |
| 4,851,046 A * | 7/1989 | Low et al. ............. 106/35 |
| 4,920,082 A * | 4/1990 | Danielson ............. 501/59 |
| 5,037,639 A | 8/1991 | Tung |
| 5,120,340 A | 6/1992 | Ducheyne et al. |
| 5,204,106 A | 4/1993 | Schepers et al. |
| 5,236,458 A | 8/1993 | Ducheyne et al. |
| 5,268,167 A | 12/1993 | Tung |
| 5,296,026 A | 3/1994 | Monroe et al. |
| 5,314,474 A | 5/1994 | Helms et al. |
| 5,340,776 A * | 8/1994 | Paschke et al. ............. 501/11 |
| 5,356,951 A | 10/1994 | Yearn et al. |
| 5,425,771 A | 6/1995 | Helms et al. |
| 5,427,768 A | 6/1995 | Tung |
| 5,429,996 A | 7/1995 | Kaneko |
| 5,432,130 A * | 7/1995 | Rheinberger et al. ......... 501/32 |
| 5,571,502 A | 11/1996 | Winston et al. |
| 5,603,922 A | 2/1997 | Winston et al. |
| 5,605,675 A | 2/1997 | Usen et al. |
| 5,614,175 A | 3/1997 | Winston et al. |
| 5,628,429 A | 5/1997 | Usen et al. |
| 5,641,347 A * | 6/1997 | Grabowski et al. ......... 106/35 |
| 5,645,853 A | 7/1997 | Winston et al. |
| 5,735,942 A * | 4/1998 | Litkowski et al. ............. 706/35 |

(List continued on next page.)

FOREIGN PATENT DOCUMENTS

| | | | |
|---|---|---|---|
| WO | 96/10985 | * | 4/1996 |
| WO | 96/00536 | | 11/1996 |
| WO | 97/27148 | * | 7/1997 |
| WO | 99/13582 | | 3/1999 |
| WO | 99/13852 | * | 3/1999 |
| WO | 99 51196 | | 10/1999 |

OTHER PUBLICATIONS

Gortner, R. A., et al., "Some Effects of Dietary Oxalate on the Teeth of White Rats", *J. Nutr.*, 32: (2) 121–131, 1946.

Greenhill, J. D., et al., "The Effects of Desensitizing Agents on the Hydraulic Conductance of Human Dentin in vitro", *J. Dental Res.*, 60: (3) 686–698, 1981.

Hench, L. L., et al., "Bonding Mechanisms at The Interface of Ceramic Prosthetic Materials"., *J. Biomed. Mater. Res. Symposium*, 5: (2:1) 117–141, 1971.

Hench, L. L., et al., "Biological Applications of Bioactive Glasses," *Life Chemistry Reports*, vol. 13, pp. 187–241 (1996).

Kaminske K, et al., "Effects of Oxalate and Calcium Phosphate Solutions on Dentin Tubule Obstruction", *J. Dent. Res.*, 69: 168, Col. 480, 1990.

Kanapka, J. A., "Over–the–Counter Dentifrices in the Treatment of Tooth Hypersensitivity", *Dent. Clin. North Am.*, 34: (3) 545–560, 1990.

Knight, N. N., et al., "Hypersensitive Dentin: Testing of Procedures for Mechanical and Chemical Obliteration of Dentinal Tubuli", *J. Periodont.*, 64: (5) 366–373, 1993.

Muzzin, K. B., et al., "Effects of Potassium Oxalate on Dentin Hypersensitivity in Vivo", *J. Periodont.*, 60: 151–158, 1989.

Pashley, D. H., et el., "Effects of the Degree of Tubule Occlusion on the Permeability of Human Dentine In Vitro", *Arch. Oral. Biol.*, 23: 1127–1131, 1978.

Pashley, D. H., et al., "Dentin Permeability*, Effects of Desensitizing Dentifrices in Vitro", *J. Periodont.*, 55: (9) 522–525, 1984.

Pashley, D. H., et al., "The Effects of Oxalate Treatment on the Smear Layer of Ground Surfaces of Human Dentine", *Arch. Oral Biol.*, 30: 731–737, 1985.

Piotrowski, G., et al., "Mechanical Studies of the Bone Bioglass Interfacial Bond," *J. Biomed. Mater. Res. Symposium*, No. 6, pp. 45–61 (1975).

Stoor, P., et al., "Interactions Between the Frontal, Sinusitis–Associated Pathogen *Haemophilus Influenzae* and the Bioactive Glass S53P4", *Bioceramics*, 8: 253–258, 1995.

Stanley, H. R., et al., "Residual alveolar ridge maintenance with a new endosseous implant material", *J. Prosthetic Dent.*, 58: (5) 607–613, 1987.

*Primary Examiner*—Shep K. Rose
(74) *Attorney, Agent, or Firm*—Burns, Doane, Swecker & Mathis, LLP

(57) ABSTRACT

Methods for whitening teeth including contacting teeth with an effective amount of particulate bioactive glass are disclosed.

14 Claims, No Drawings

U.S. PATENT DOCUMENTS

| | | |
|---|---|---|
| 5,741,479 A | 4/1998 | Masterman et al. |
| 5,766,328 A | 6/1998 | Nakabayshi et al. |
| 5,817,296 A | 10/1998 | Winston et al. |
| 5,833,957 A | 11/1998 | Winston et al. |
| RE36,035 E | 1/1999 | Usen et al. |
| 5,858,333 A | 1/1999 | Winston et al. |
| 5,860,565 A | 1/1999 | Winston et al. |
| 5,866,102 A | 2/1999 | Winston et al. |
| 5,895,641 A | 4/1999 | Usen et al. |
| 6,086,374 A * | 7/2000 | Litkowski et al. ........ 433/217.1 |
| 6,190,643 B1 * | 2/2001 | Stoor et al. .................... 424/49 |

* cited by examiner

METHODS AND COMPOSITIONS FOR WHITENING TEETH

This application is a continuation of International Application No. PCT/US98/18500 filed on Sep. 18 1998, which designates the United States and claims priority under 35 U.S.C. §§ 119 and/or 365 to 60/059,222 filed in United States of America on Sep. 18, 1997.

FIELD OF THE INVENTION

The present invention relates to methods for whitening, lightening, bleaching or removing stains from teeth using certain bioactive glass compositions.

BACKGROUND OF THE INVENTION

A tooth is comprised of an inner dentin layer and an outer hard enamel layer that is the protective layer of the tooth. The enamel layer of the tooth is naturally an opaque white or slightly off-white color. It is this enamel layer that can become stained or discolored. The enamel layer of the tooth is composed of hydroxyapatite mineral crystals that create a somewhat porous surface. It is believed that this porous nature of the enamel layer is what allows staining agents and discoloring substances to permeate the enamel and discolor the tooth. In addition, the tooth naturally acquires a film called pellicle, made up of salivary glycoproteins. The pellicle may also acquire stain. As the terms "tooth" or "teeth" are used herein, they are intended to mean a material which is apatite and the acquired pellicle.

Many substances that a person confronts or comes in contact with on a daily basis can "stain" or reduce the "whiteness" of one's teeth. In particular, the foods, tobacco products and fluids such as tea and coffee, that one consumes tend to stain one's teeth. These staining and discoloring substances can then permeate the enamel layer. This problem occurs gradually over many years, but imparts a noticeable discoloration of the enamel of one's teeth.

WO 96/10985 discloses particulate bioactive silica containing glasses that can reduce pulpal irritation of a tooth and/or strengthen the structure of a tooth and therefore have use in the treatment of hypersensitive teeth. It is suggested that such glasses can consist solely of silicon oxide or silicon hydroxide or can contain one or more additional elements selected from Ca, P, Na, K, Al, B, N, Mg, Ti, or F. It is also suggested that it is advisable to use bioactive glass compositions comprising calcium and phosphate which can help induce remineralisation of dentin or alternatively to use separate sources of calcium and phosphate together with a bioactive glass not containing them.

WO 97/27148 discloses particulate bioactive and biocompatible glasses which can remineralise teeth and are of particular use in the reduction of dentin hypersensitivity.

Various treatment modalities have been used to whiten teeth including in-office bleaching, night guard bleaching and whitening toothpastes. However, the available methods and compositions are not satisfactory for a variety of reasons. For example, shade reduction has been less than ideal.

SUMMARY OF THE INVENTION

It has now been discovered that the above-noted bioactive glasses can be used to whiten teeth. Accordingly the present invention provides a method of whitening teeth, which comprises contacting a tooth structure with a tooth-whitening amount of a particulate bioactive and biocompatible glass.

DETAILED DESCRIPTION OF THE INVENTION

These following words are intended to be given the same meaning here as would be accorded to them in their contemporary usage in the oral and dental care arts. More specific usage for the invention herein is described below.

The term "whitening" is used herein at all occurrences to include bleaching, lightening, or removing stain from the teeth.

The present invention provides a method for whitening, lightening or bleaching teeth. The method is also useful for removing stains from teeth. The method includes contacting teeth with an effective tooth-whitening amount of bioactive glass as disclosed in WO 96/10985 and WO 97/27148. Preferably, multiple applications are carried out. Each application may include between about 0.02 to 0.3 grams of bioactive glass. Suitably, the instant method of whitening teeth comprises contacting the teeth with said effective tooth-whitening amount of bioactive glass twice daily for two weeks or more. As the term "tooth-whitening amount" is used herein, it is intended to mean any amount that will result in a Vita shade guide lightening of one or more shades in a patient with a pre-treatment shade darker than A3.5 after 4 weeks of application twice daily for two minutes or more per application.

Accordingly the present invention provides a method for whitening teeth which comprises contacting teeth with an effective tooth-whitening amount of particulate bioactive and biocompatible glass comprising silicon oxide or hydroxide and optionally one or more elements selected from Na, K, Ca, Mg, B, Ti, Al, P, N or F.

Preferably the bioactive glass comprises at least Na, Ca and P, although it is possible to use simple sodium silica glasses together with external sources of calcium and phosphate. It will be understood by the skilled artisan that an external source of calcium and phosphate may be from saliva itself, or may be formulated into the oral hygiene composition.

A bioactive glass in accordance with the present invention is a glass composition that will form a layer of hydroxycarbonate apatite in vitro when placed in a simulated body fluid. Bioactive glasses in accordance with the present invention may be prepared by a variety of processes, e.g., melt-derived or sol gel and may have a variety of compositional elements and ranges. For example, the following composition by weight will provide an acceptable and preferred bioactive glass:

| | |
|---|---|
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 |
| $K_2O$ | 0–8 |
| MgO | 0–5 |

Bioactive glasses with these properties provide a more efficacious material for interaction with the tooth structure. The addition of fluoride in the glass composition will enhance and strengthen the tooth structure. Other examples include sol gel glasses having, for example, about 40 to about 86% by weight $SiO_2$, substantially no amount of sodium, about 6–36% by weight Ca and about 2–12% by weight $P_2O_5$. A biocompatible glass in accordance with the present invention is one that does not trigger an overwhelmingly adverse immune response.

In, some embodiments of the present invention, extremely small particles are used. For example, particles that are in the range of 2 mm to submicron are beneficial. Particle size in accordance with the present invention is determined by scanning electron microscopy or laser light scattering techniques (e.g., Coulter LS100). Surprisingly, the relatively small bioactive particulate glass does not generate a significant immune response. Moreover, it is generally not engulfed by macrophages and rendered inactive in this application.

The compositions of the present invention may be formulated as oral hygiene compositions such as dentifrices, toothpaste, gels, powders, mouthwashes, irrigating solutions, and presentations for sucking or chewing such as gums, pastilles, tablets, and lozenges.

Such oral hygiene compositions suitably comprise between 0.1 to 50% by weight, preferably 1 to 25% by weight, more preferably 5 to 10% by weight of the bioactive glass.

In addition to the active ingredients, the oral hygiene compositions suitable for this invention will contain the usual carriers, binders, surfactants, humectants, coloring agents, pigments, antiplaque agents, anti-bacterial agents, bioadhesive-type agents, abrasives, anticaries agents, flavorings, sweeteners, bulking agents, and the like.

In the case of a toothpaste formulation, an abrasive typically includes amorphous, gelled, precipitated, or fumed silica, plastics particles; alumina, calcium carbonate, and zinc orthophosphate, insoluble metaphosphates and calcium pyrophosphate. Silica is an especially preferred abrasive for use herein. The patent and scientific literature is replete with examples of such abrasives. U.S. Pat. No. 4,822,599 listing a series of dentifrice abrasives also references commercial sources and methods for their preparation. The bioactive glass particles may replace all, some, or none of the abrasive currently used in toothpastes.

Inorganic thickeners may be included in the dentifrices of the present invention and include fumed silicas such as Cabosil available from Cabot Corporation, and thickening silicas including those available from J. M. Huber designated Zeodent 165. Organic thickeners such as natural and synthetic gums and colloids may also be incorporated in the dentifrice composition of the present invention. Examples of such thickeners include carrageenan (Irish moss), xanthan gum and sodium carboxymethyl cellulose, starch, polyvinlpyrrolidone, hydroxyethyl propyl cellulose, hydroxbutyl methyl cellulose, hydroxypropyl methyl cellulose, and hydroxyethyl cellulose (co-dried blends of microcrystalline cellulose/cellulose gum). The inorganic or organic thickener may be incorporated in the compositions of the present invention at a concentration of about 0.05 to about 2% by weight and preferably about 0.1 to about 1.5% by weight.

Fluoride-providing salts having anti-caries efficacy may also be incorporated in the oral compositions of the present invention and are characterized by their ability to release fluoride ions in water. It is preferable to employ a water-soluble salt fluoride providing about 10 to 5,000 ppm of fluoride ion and preferably about 1000 to 1500 ppm of fluoride ion. Among these materials are water-soluble alkali metal salts, for example, sodium fluoride, potassium fluoride, sodium monofluorophosphate and sodium fluorosilicate. Sodium monofluorophosphate is the preferred fluoride-providing salt.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C Yellow #15 lake. The pigments have a particle size in the range of 5–1000 microns, preferably 250–500 microns, and are present at a concentration of 0.5 to 3% by weight. Dyes are generally sensitive to the presence of the peroxide ingredient and are not included in the dentifrice although FD&C Green #3 has been found to be resistant to fading when $CaO_2$ is present in the dentifrice.

Any suitable flavoring or sweetening material may be employed. Examples of suitable flavoring ingredients are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and sodium saccharin. Suitably, flavor and sweetening agents may together comprise from 0.01% to 5% or more of the preparations.

Various other materials may be incorporated into the oral composition components of this invention. Non-limiting examples thereof include preservatives, silicones and chlorophyll compounds, vitamins such as vitamins B6, 1312, C, E and K, antibacterial agents such as chlorhexidine, halogenated diphenyl ethers such as triclosan, desensitizing agents such as potassium nitrate and potassium citrate and mixtures thereof. These adjuvants are incorporated in the dentifrice in amounts which do not substantially adversely affect the properties and characteristics desired, and are selected and used in proper amounts, depending upon the particular type of component involved.

The making of particulate bioactive glasses are well known to those of ordinary skill in the art and need no further description here. Similarly, the making of gels, toothpastes, rinses, mouthwashes, gums, chewing gums are also well known in the art. Bioactive glasses can be introduced into these products by a variety of methods including simple mixing. Those of ordinary skill in the art will appreciate that in some circumstances it will be necessary to keep the bioactive glass from coming into contact with the aqueous or other components of the delivery vehicle to prevent the bioactive glass from pre-reacting. This can be accomplished by a variety of ways known to those of ordinary skill in the art including, for example, two piece syringes with a mixing chamber.

In addition to direct application of the bioactive glass to the teeth, the bioactive glass composition of the present invention can also be applied in a saline or distilled water based medium.

The present invention also provides the use of a bioactive and biocompatible glass as herein before defined optionally together with a source of calcium and/or phosphate in the manufacture of a composition for whitening teeth.

EXAMPLE

Ten healthy adult volunteers were screened for acceptance into this 4-week clinical trial. At baseline, the shade measurement was taken from the middle third to the incisal edge with a Vita shade guide arranged in the following order: B1, A1, B2, D2, A2, C1, C2, D4, A3, D3, B3, A3.5, B4, C3, A4, C4 (Lumin Vacuum-Farbskala, Vita). Only patients with shade no lighter than A3.5 were qualified for this study. Condition of hard tissue and soft tissue were noted for each subject prior to and at each study appointment. Patients were instructed to use only 7.5% dentifrice two times daily, maintain 2 minutes brushing time and to abstain from other oral care products. All subjects were recalled at two and four weeks.

At two weeks the mean shade tabs change was 4.2 with a range from 0 to 8. At four weeks the mean shade tabs changes was 5.8 with a range from 0–8. No deleterious effects on the hard tissue and soft tissue were noted. Statistic analysis demonstrated that a significant difference between both two weeks and four weeks and baseline ($p<0.05$), ANOVA). In conclusion, 7.5% dentifrice was shown to whiten the teeth with a mean shade change of 5.8 with no adverse effect. This study was supported in part by USBiomaterials Corporation.

The 7.5% dentifrice as described in the Example included 7.5% by weight of a bioactive glass having the following composition:

| | |
|---|---|
| $SiO_2$ | 45 |
| CaO | 24.5 |
| $Na_2O$ | 24.5 |
| $P_2O_5$ | 6 |

We claim:

1. A method for whitening teeth comprising contacting teeth in need of whitening with an effective tooth-whitening amount of particulate bioactive and biocompatible glass daily until such time as said teeth are lightened at least one shade on a Vita shade guide, the particulate bioactive and biocompatible glass comprising silicon oxide or hydroxide and optionally one or more elements selected from Na, K, Ca, Mg, B, Ti, Al, P, N or F.

2. A method according to claim 1 wherein the bioactive and biocompatible glass comprises at least Na, Ca and P.

3. The method of claim 1 wherein the bioactive and biocompatible glass is administered together with a source of calcium and/or phosphate.

4. The method of claim 1 wherein the bioactive and biocompatible glass includes by weight percentage:

| | |
|---|---|
| $SiO_2$ | 40–60 |
| CaO | 10–30 |
| $Na_2O$ | 10–35 |
| $P_2O_5$ | 2–8 |
| $CaF_2$ | 0–25 |

-continued

| | |
|---|---|
| $B_2O_3$ | 0–10 |
| $K_2O$ | 0–8 |
| MgO | 0–5. |

5. The method of claim 1, wherein said particulate bioactive and biocompatible glass includes particles less than about 90 mm.

6. The method of claim 1, wherein said particulate bioactive and biocompatible glass includes particles less than about 10 mm.

7. The method of claim 1, wherein said particulate bioactive and biocompatible glass includes particles less than about 5 mm.

8. The method of claim 1 wherein said particulate bioactive and biocompatible glass includes particles less than about 2 mm.

9. The method of claim 1, wherein said effective amount is about 0.02 to about 0.3 grams.

10. The method of claim 1 wherein the particulate glass is in a toothpaste or gum.

11. A method for whitening teeth comprising contacting teeth with an effective shade reducing amount of particulate bioactive and biocompatible glass as defined in the method of claim 1.

12. A tooth-whitening oral hygiene composition comprising an effective tooth-whitening amount of particulate bioactive and biocompatible glass as defined in the method of claim 1.

13. The method of claim 1 wherein the teeth have a Vita shade no lighter than A3.5 and the teeth are contacted with the effective tooth-whitening amount of particulate bioactive and biocompatible glass at least two times daily for a period of two weeks or more such that a Vita shade guide lightening of one or more shades results.

14. The method of claim 13 wherein the teeth are contacted with the effective tooth-whitening amount of particulate bioactive and biocompatible glass for two minutes or more each time the teeth are contacted.

* * * * *